United States Patent [19]

Sabee

[11] 4,227,952
[45] Oct. 14, 1980

[54] METHOD AND APPARATUS FOR MAKING DIAPERS WITH ELASTIC BANDS

[75] Inventor: Reinhardt N. Sabee, Appleton, Wis.
[73] Assignee: Sabee Products, Inc., Appleton, Wis.
[21] Appl. No.: 30,584
[22] Filed: Apr. 16, 1979
[51] Int. Cl.[2] .............................................. B32B 31/08
[52] U.S. Cl. .................................... 156/164; 156/204; 156/250; 156/270; 156/290; 156/474; 156/494; 156/516
[58] Field of Search ................ 156/160, 163–164, 156/152, 196, 199, 204, 205, 207, 210, 226, 227, 250, 264, 265, 269–270, 290–292, 470, 443, 494, 459, 516, 522, 474

[56] References Cited

U.S. PATENT DOCUMENTS

| | | | |
|---|---|---|---|
| 1,544,312 | 6/1925 | Gray | 156/163 X |
| 2,926,720 | 3/1960 | Grosman | 156/470 X |
| 3,457,137 | 7/1969 | McCarthy | 156/152 X |
| 3,829,344 | 8/1974 | Julev et al. | 156/474 X |
| 3,860,003 | 1/1975 | Buell | 128/287 |
| 4,081,301 | 3/1978 | Buell | 156/291 X |

Primary Examiner—David A. Simmons
Attorney, Agent, or Firm—Henry C. Fuller

[57] ABSTRACT

Method and apparatus for making diapers with elastic bands in the leg-contacting zone of the diaper involves forming folds, tucks or festoons in the diaper backing sheet or facing sheet and applying elastic ribbon treated with adhesive over the web and across the gaps of the folds so that the ribbon does not adhere to the web portion in the folds. Hence the elastic ribbon is only adhered to the portions of the web between the folds. The elastic ribbons are cut in the gaps of the folds, with the material in the folds later forming the nonelasticized waistband portion of the diapers. At the ribbon-web assembly station, the facing or backing sheet is supported by spaced plates separated by gaps. Before the ribbon is applied, the folds are formed by tucker bars which successively interfit in the gaps between the support plates and push the web into the gaps.

10 Claims, 10 Drawing Figures

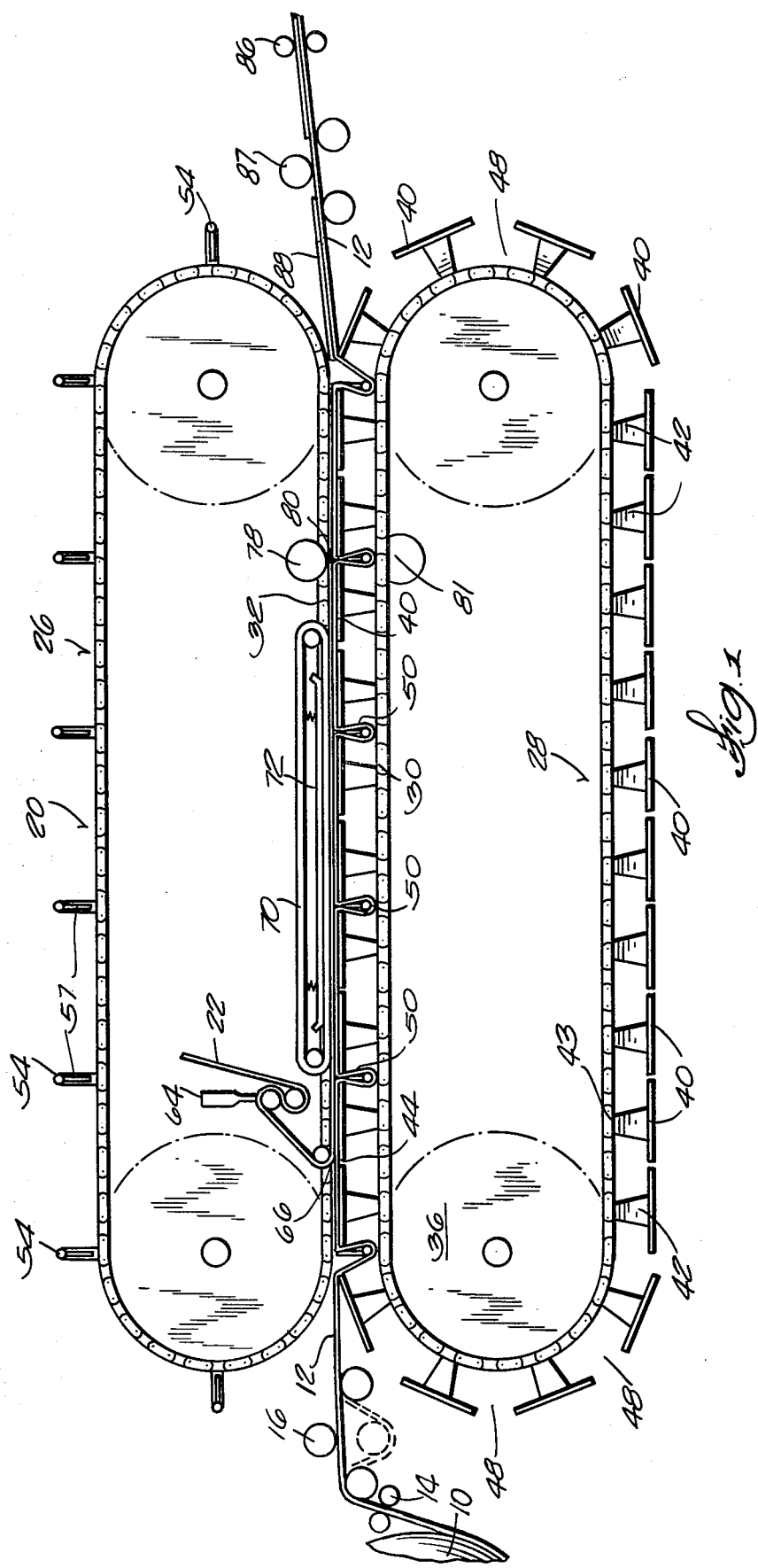

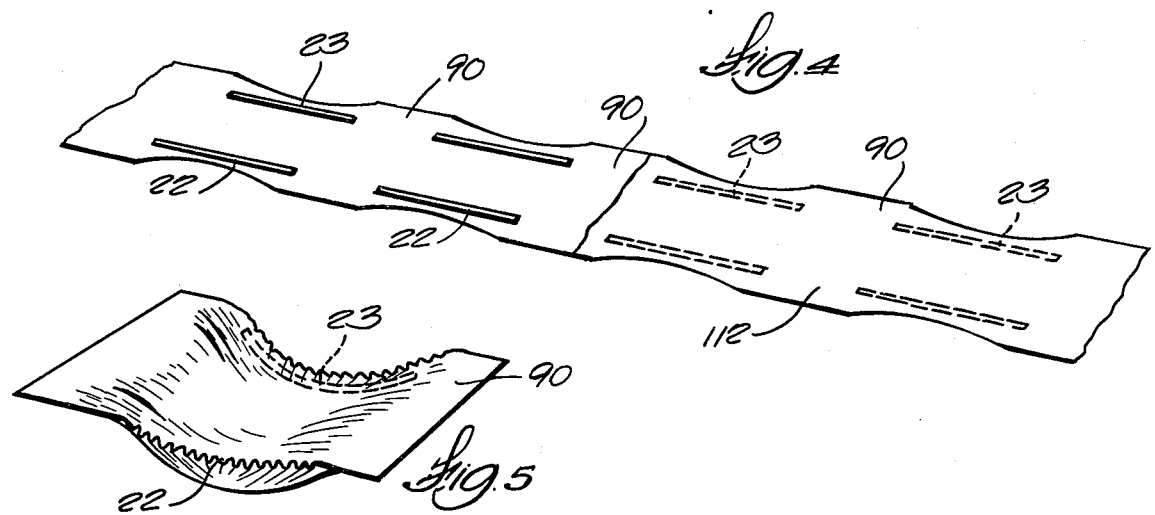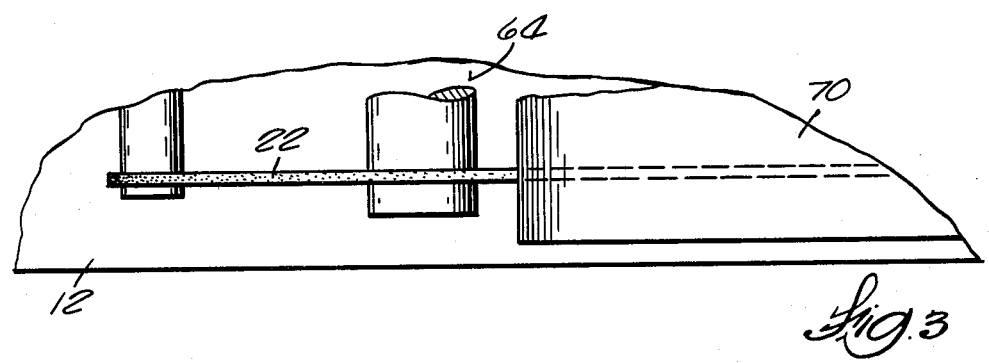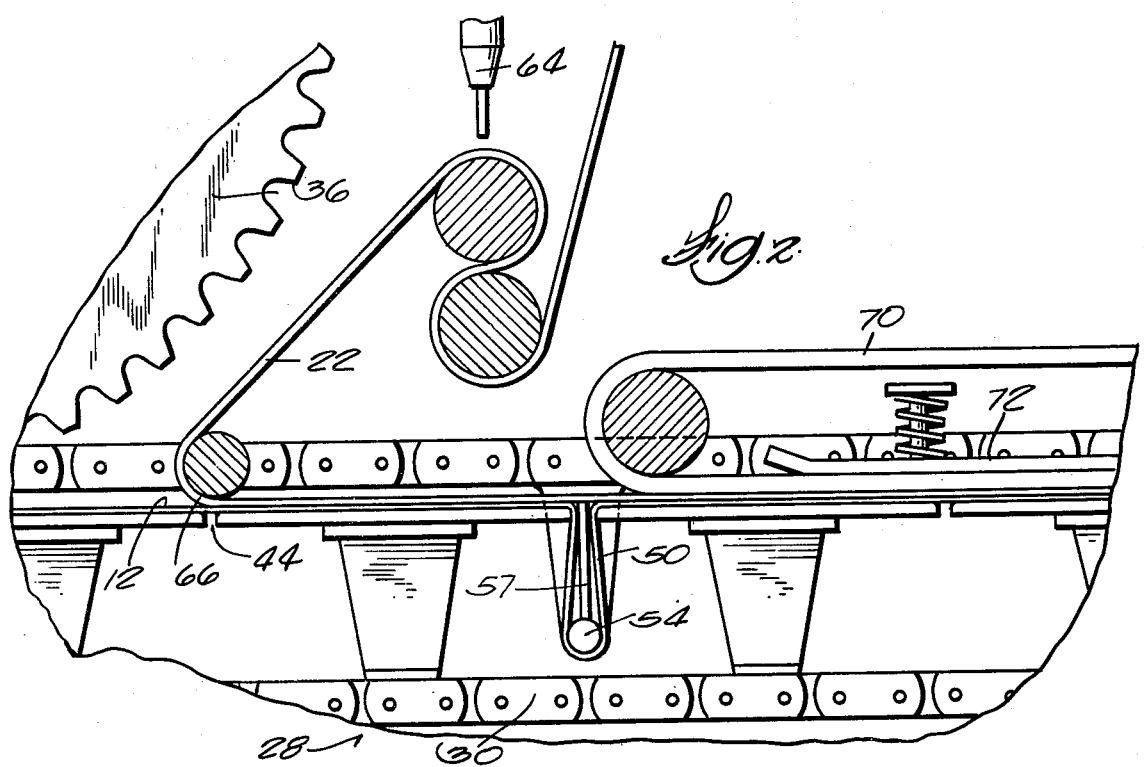

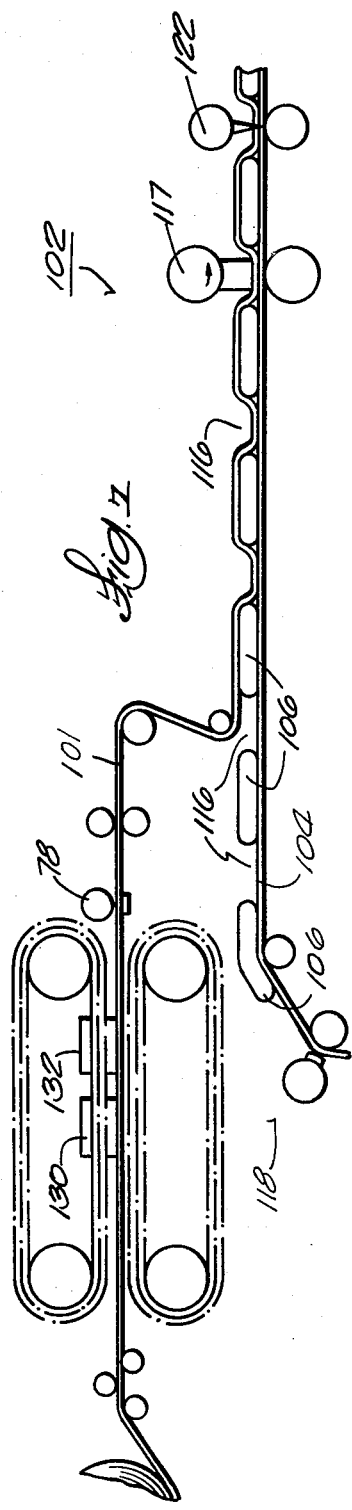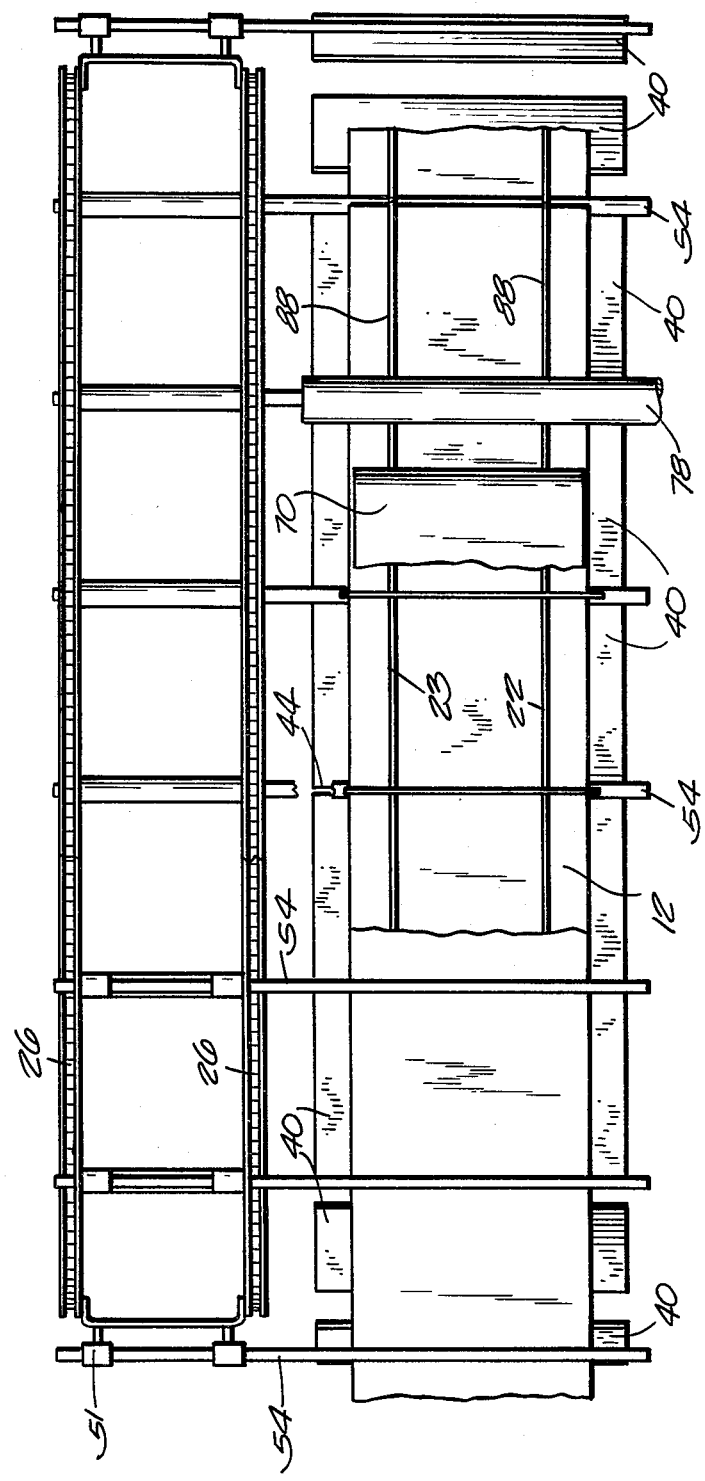

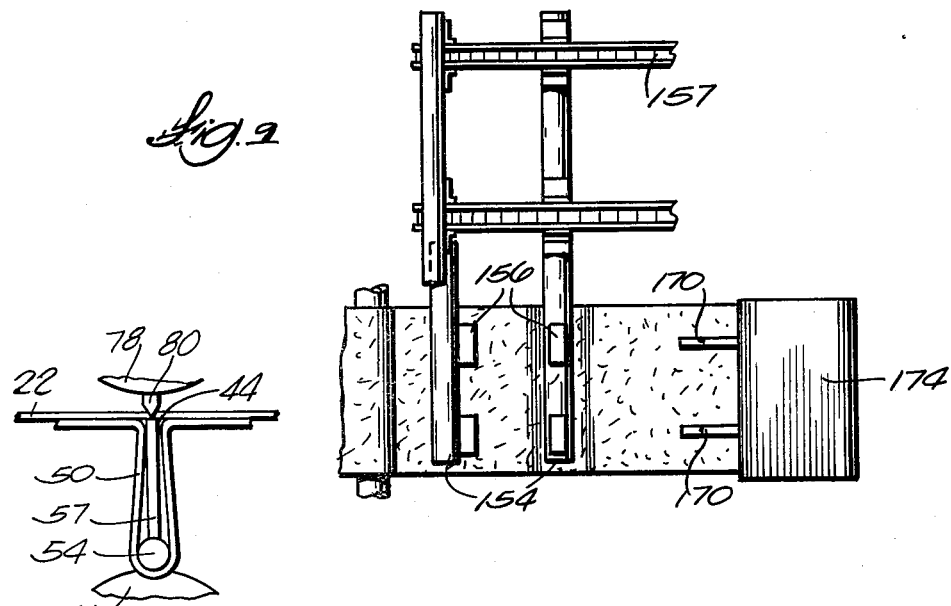
Fig. 9
Fig. 10
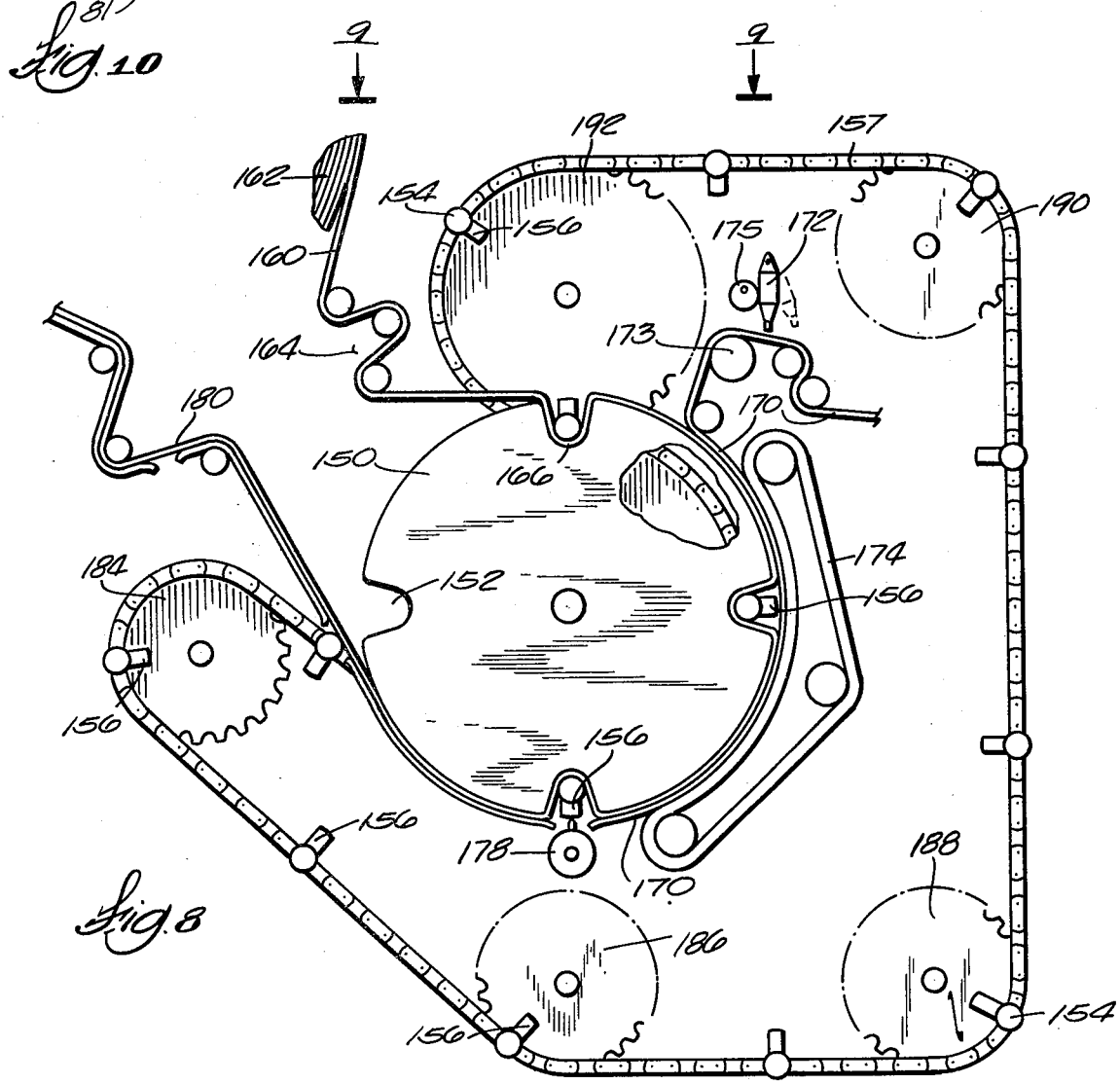
Fig. 8

METHOD AND APPARATUS FOR MAKING DIAPERS WITH ELASTIC BANDS

BACKGROUND OF THE INVENTION

The present invention relates to method and apparatus for making a diaper and a new diaper construction. U.S. Pat. No. 3,860,003 discloses a diaper construction with elastic strips adhesively secured to the backing sheet of a diaper to provide a close fit of the diaper to the baby's legs. The elastic ribbon provides elastically contractable leg openings. U.S. Pat. No. 4,081,301 discloses apparatus for making diapers of the type disclosed in U.S. Pat. No. 3,860,003. In a diaper construction of the type exemplified by U.S. Pat. No. 3,860,003, it is desirable that the elastic be only in the leg-contacting diaper portions rather than in the waistband portions. Accordingly, the elastic band is only adhered to the facing or backing sheet in the leg-contacting zone of the diaper. To accomplish this result, glue is intermittently applied to the continuously fed elastic band so that it will adhere to the desired leg-contacting portion of the diaper but not the waistband portions of the diaper. Inasmuch as the elastic bands are superimposed on the backing as a continuous ribbon, the bands extend to the ends of the diaper. When the diapers are cut from the web, the tension on the non-glued portions of the elastic bands adjacent the cuts is relaxed and the ends of the bands contract. The non-adhering portions of the elastic ribbon provide or serve no useful function in the completed diaper and constitute considerable waste of ribbon. The wasted portion of the ribbon can constitute as much as 40% of the total length of ribbon used per diaper.

SUMMARY OF THE INVENTION

The invention provides method and apparatus for pre-applying two elastic ribbons or bands to either the moisture impervious backing or the moisture pervious top sheet in advance of assembly of the absorbent material top sheet and backing at the assembly station where the diaper is formed. More specifically, the elastic ribbon and web to which the ribbons will be affixed are continuously fed to an elastic band applying station. Adhesive is supplied to the entire lengths of elastic ribbon prior to superimposing the ribbon on the web. The web is folded at spaced intervals by forming festoons to prevent portions of the elasticized band from contacting the adhesive bearing elastic band. The folds in the web which do not have an adhesively adhered portion of elastic ribbon later become the non-elasticized waistband portions of the diapers. The festoons or folds are formed by feeding the web top sheet or backing sheet to a conveyor which carries spaced web support plates carried by chains which form a substantially planar and continuous surface when the chains are making an upper horizontal run. However, as the chain winds around the end sprockets just prior to the horizontal run, the plates separate slightly to form a break in the web-supporting surface. As the support plates approach the horizontal supporting run and come into contact with the incoming web, spaced tucker bars carried by an offset chain continuously and successively push the web downwardly between the spaced web supporting plates.

Thus a series of festoons or folds in the web are continuously and sequentially formed at spaced intervals by the tucker bars in gaps between plates. As the support plates move along the horizontal supporting run, the plates come together with only a minor gap separating the adjacent ends. The loops or folds of the facing sheet are confined within the gap and wrapped around the ends of the tucker bars. Two spaced elastic bands or ribbons under tension and with adhesive applied are fed into the system and superimposed on the facing sheet over the gaps above the folds or festoons. Continued movement of the facing sheet and elastic bands takes the facing sheet and bands under a hold-down belt with a pressure plate which sets the adhesive. the elastic bands are severed in the gaps between the support plates by a rotary cut-off knife or the like which moves in sequence and cuts the elastic band. Inasmuch as the elastic band is cut by the knife in a gap where the web is folded, with the bight of the fold substantially below the ribbon, the web itself is not cut, only the elastic ribbon.

The foregoing method and apparatus result in minimal waste of elastic ribbon and provide a method for pre-application of ribbon to the backing sheet which can be stored for later use or immediately delivered to the diaper assembly station.

Further objects, advantages and features of the invention will become apparent from the disclosure.

DESCRIPTION OF THE DRAWINGS

FIG. 1 is a diagrammatic side elevational view of apparatus for performing the method of the invention.

FIG. 2 is an enlarged view of a portion of FIG. 1.

FIG. 3 is a fragmentary plan view of apparatus shown in FIG. 2.

FIG. 4 is a perspective view of the web with elastic ribbons applied in accordance with the invention.

FIG. 5 is a perspective view of a single diaper.

FIG. 6 is a fragmentary enlarged plan view of the apparatus illustrated in FIG. 1.

FIG. 7 is a diagrammatic side elevational view of an elastic ribbon applying station and a diaper forming station.

FIG. 8 is a modified embodiment of apparatus to practice the invention.

FIG. 9 is a view along line 9—9 of FIG. 8.

FIG. 10 is an enlarged view of the cut-off knife shown in FIG. 1.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

The illustrated apparatus will be described relative to a process for forming disposable diapers. However, the apparatus and method disclosed herein are suitable for applying ribbons of elastic to a web for other garments or products. As disclosed, a parent or supply roll 10 supplies a web 12 which can be either the facing sheet which is absorbent or a non-absorbent or impervious backing sheet for a diaper. Feed rolls 14 provide a velocity V-1 higher than the velocity of the web in the elastic ribbon applying station, as subsequently described. This provides slack which is used to form fold or festoons. Dancer rolls 16 control the slack.

The web 12 is fed to a ribbon applying or combining station 20. At the ribbon combining station 20, two ribbons or bands 22, 23 of elastic material are superimposed on the web 12 while in a stretched condition under tension. The stretched elastic bands 22, 23 are applied continuously to the web 12 and over the gaps where festoons or folds are formed.

In this regard, the combining station 20 includes upper and lower conveyor chain pairs 26 and 28 which are laterally offset as shown in FIG. 6. Chains 28 are arranged around sprockets 36, with the spaced chains 28 carrying a plurality of web support plates 40 which are connected to the chains by brackets 42 having suitable chain connectors 43 (not described in detail). The support plates 40 are arranged and spaced on the chains 28 so that they form a substantially continuous supporting surface when in the upper run position 30 (FIG. 1), with the support plates 40 separated by small gaps 44. However, as the chain 28 traverses the radius of the sprockets 36, the plates 40 spread and form larger gaps 48 (FIG. 1). It is through the gaps 48 that folds, festoons or tucks 50 are formed as presently described.

As illustrated in FIGS. 1 and 6, chain pair 26 is laterally offset from chain pair 28 and carries a plurality of tucker bar supports 51 which carry tucker bars 54. The tucker bars project laterally to register with the gaps 48 between the support plates 40 and push the web 12 into the gaps 48 to form folds 50 in sequence. Each tucker bar 54 is provided with a longitudinally extending fin 57 or anvil bar which cooperates with the ribbon cut-off knife 78 as presently described.

The elastic ribbons 22, 23 are applied in a stretched condition under tension to the web 12 at 66 (FIG. 2). Adhesive is continuously supplied to the ribbons 22, 23 by a glue applicator 64 prior to contact of the ribbons 22, 23 with the web 12. A hold-down belt 70 with a pressure plate 72 firmly applies the ribbons to the web 12 and maintains the contact of the elastic ribbons 22, 23 and web 12 until the adhesive sets.

As illustrated in FIG. 10 the elastic ribbons 22, 23 are severed in the small gaps 44 between the support plates 40 by a rotary cut-off knife 78 which is timed to apply the cutting edge 80 to the ribbons within the small gaps 44 above the bights of the folds or festoons so that the web 12 is not also severed. An anvil back-up or support roller 81 can be provided.

Draw rolls 86 withdraw the web 12 and superimposed elastic strips 88 from the combining unit 20 and the festoons or folds 50 are removed as the slack in the web is taken out by the dancer rolls 87 to result in gaps 90 on the web 12 between adjacent ends of the elastic band or ribbon. The web 12 (FIG. 4) with the spaced and stretched elastic leg band portions can then be stored or fed to a station for combining the web and absorbent pad and top or backing sheet to form a diaper. The draw rolls 86 increase the velocity of the web 12 to a velocity greater than that in the combining unit to remove the folds or festoons. Inasmuch as the elastic bands are assembled and maintained under tension, upon release of the tension when a diaper is cut from the diaper chain, the relaxed elastic bands will cause the diaper to bunch up as shown in FIG. 5.

The composite 101 of elastic ribbons and web 12 include portions 90 which form the waistband portion of the diaper and which are free of elastic band. Thus there is no waste of unused elastic band material as there is in the prior art diapers such as that disclosed in the U.S. Pat. No. 3,860,003, hence reducing the cost of the diaper. The width of the waistband portions 90 which is non-elasticized is determined by the depth of the festoons or folds 50 and the radius of the tucker bar 54. The length of the stretched ribbon is equal to the distance between festoons. The size of the festoons or folds can be varied for the particular application. Small festoons will provide a greater percent of elasticized length, with large festoons resulting in a smaller percentage of elasticized length. Hence, varying the festoon size determines the length of the attached elastic band.

The web in FIG. 4 can be delivered immediately to a diaper assembly station 102 shown in FIG. 7. At the diaper forming station 102, a second web 104 which comprises either a backing sheet or facing sheet, depending on the character of web 90, carries spaced apart absorbent pad elements 106 which are assembled in a lamina with sheet 101 which contains the elastic bands 22, 23. The assembly is synchronized so that the gaps 112 between the ends of the bands are centered between the pads so that there is no elastic in the waistband portions 90 (FIG. 5) of the diapers. The lamina of web 101 and web 104 can be glued by equipment 118 to form a chain of diapers which are separated in the waistband portions by a cut-off knife 122 after being secured by a press bar 117.

In the embodiments of the apparatus shown in FIGS. 1 and 2, an adhesive is applied to secure the ribbon to the web. Alternatively, the adhesive can be a hot melt adhesive with a heater and cooling unit to process the adhesive. The ribbons 22, 23 can be heat sealed to the web by a heat seal unit rather than by the use of adhesive.

FIGS. 8 and 9 show a modified embodiment of the apparatus of the invention. In the modified embodiment, the folds are formed on a grooved roller 150 which has equally spaced grooves 152. Festoon, tucker or fold forming bars 154 having anvil surfaces or anvil blocks 156 are carried by spaced chains 167 about a tortuous circuit.

The web 160 of facing or backing material for diapers is drawn from a parent roll 162 and controlled by dancer rolls 164. The web is fed to the roll 150 at a velocity $V_1$ higher than the velocity $V_2$ of the peripheral surface of the roll 150. The tucker bars register with the grooves 152 and push the web 160 into the groove 152 to form a fold or festoon 166.

Spaced elastic bands 170 are delivered to the backing or facing sheet web 160 after glue is applied by glue applicator 172. A vacuum or friction roll 173 can be employed to stretch the ribbons after adhesive is applied. The adhesive applicator can be operated by a cam 175 or other timing device so that adhesive is not applied in the ribbon severing zones, thus reducing the quantity of adhesive required. One or more hold-down belts 174 retain the stretched elastic bands 170 against the web 160 until the adhesive sets. The elastic bands 170 are severed in the folds with or by rotary cut-off knives 178 which cooperate with the anvil 156 of each tucker bar. As the web 160 leaves the roll 150, the web is accelerated from velocity $V_2$ to velocity $V_1$ to remove the folds. The web leaves dancer rolls 180 and travels to the diaper assembly station (not shown).

The chains carrying the tucker bars 154 are arranged around sprockets 184, 186, 188, 190 and 192. The sprockets are arranged to maintain the tucker bars in position with the grooves 152 in the roll 150 for a major portion of the periphery of the rolls, as illustrated, to accomplish the application and cutting of the elastic bands or ribbon 170.

It is apparent that additional cost savings can be obtained if the adhesive is applied intermittently to the elastic ribbon, such as in the form of spaced dots rather than continuously. The length and extent of the adhesive application can be varied and adhesive need not be applied in ribbon severing zones as pointed out above.

The unit length of the web for one diaper or article to which the ribbon is applied is always longer than the unit length of the applied ribbon under tension for one diaper or article because of the tucks or folds in the web.

What is claimed is:

1. A method for continuously attaching discrete lengths of elastic ribbon to spaced portions of a moving web comprising the steps of:
   (a) continuously moving a web of substantially inelastic material through an elastic ribbon applying station;
   (b) forming transverse folds at spaced locations along said web;
   (c) feeding stretched elastic ribbon to said web;
   (d) applying adhesive to the stretched elastic ribbon;
   (e) joining the stretched elastic ribbon with adhesive to said web and over the folds;
   (f) maintaining the elastic ribbon in a stretched condition until the adhesive sets;
   (g) severing the elastic ribbon where the ribbon crosses the folds; and
   (h) removing the folds from the web to space apart the ends of the severed elastic ribbons and provide web portions without adhered elastic bands to form the waistband portions of the diapers.

2. A method for continuously attaching discrete lengths of elastic ribbon to isolated portions of a moving, substantially inelastic web to impart an elasticized character thereto while preserving the substantially inelastic character thereof in areas where said ribbon is unattached to said web, said method comprising the steps of:
   (a) supplying a continuously moving web of substantially inelastic material at a first velocity;
   (b) forming festoons transversely at discrete, predetermined locations along the length of said web, thereby decreasing the velocity of the web to less than the first velocity;
   (c) feeding an elastic ribbon in a stretched condition along the length of said web;
   (d) applying adhesive to said stretched elastic ribbon;
   (e) adhering the said stretched elastic ribbon to areas between festoons of said web at the decreased velocity;
   (f) maintaining said elastic ribbon in a stretched condition until the adhesive sets;
   (g) severing the elastic ribbon in the proximity of the festoons; and
   (h) opening the festoons to space apart the elastic ribbons and increasing the velocity of said web to the first velocity.

3. A method of intermittently attaching a pair of elastic ribbons to predetermined, isolated portions of a moving, substantially inelastic web to impart an elasticized character thereto while preserving the substantially inelastic character thereof in areas where said ribbon is unattached to said web, said method comprising the steps of:
   (a) supplying at least one continuously moving web of substantially inelastic material;
   (b) feeding a heat-sealable elastic ribbon in a stretched condition;
   (c) forming transverse folds at discrete, predetermined locations along the length of said web;
   (d) adhering said heat-sealable elastic ribbon in areas between folds along the length of said web by elevating the surface temperature of said ribbon;
   (e) maintaining said elastic ribbon in a stretched condition until the temperature of said ribbon has been lowered sufficiently to bond said ribbon to said web;
   (f) severing said elastic ribbon in the proximity of the fold; and
   (g) opening said folds to space apart said elastic ribbons.

4. A method for continuously attaching discrete lengths of elastic ribbon to isolated portions of a moving, substantially inelastic web, said method comprising the steps of:
   (a) supplying a moving web of substantially inelastic material;
   (b) increasing momentarily the velocity of said incoming web to form folds;
   (c) feeding an elastic ribbon in a stretched condition along the length of said web;
   (d) applying adhesive to said stretched elastic ribbon;
   (e) adhering the said stretched elastic ribbon to the web in areas between the folds;
   (f) maintaining said elastic ribbon in a stretched condition until the adhesive sets;
   (g) severing the elastic ribbon in the proximity of the folds; and
   (h) increasing momentarily the velocity of the moving outgoing web whereby said folds are opened and the elastic ribbons are spaced apart.

5. A method of claim 4 including the subsequent step of assembling said web with a second web having spaced pads with the gaps between the ends of the pads being in registry with the gaps between the ribbons to provide diapers with waistband portions free of ribbons.

6. Apparatus for applying an elastic ribbon to spaced portions of a web comprising:
   (a) means for supplying a web to an assembly station;
   (b) means for providing a supporting surface with gaps for supporting said web at spaced points at the assembly station;
   (c) means for sequentially pushing portions of the web into said gaps to form transverse folds in said web;
   (d) means for supplying an elastic ribbon having a coating of adhesive to said web across said gaps to cause the ribbon to adhere to said web adjacent the folds, said ribbon being under tension; and
   (e) means for cutting said ribbon in said gaps without cutting the web to form a series of disconnected elastic bands with spaced ends.

7. Apparatus in accordance with claim 6 wherein said means for supporting said web at the assembly station comprises a pair of spaced chains and closely spaced support plates connected to said chains to provide a supporting surface with transverse gaps therebetween at the assembly station, and wherein said means for sequentially pushing portions of the web into said gaps to form transverse folds comprises tucker bars supported for sequential movement into the gaps between said support plates when said gaps are separated to push portions of the web into said gaps during said movement.

8. Apparatus in accordance with claim 7 wherein said cutting means comprises a rotary cutting knife which cuts the elastic ribbon in said gaps without cutting the web, and wherein said tucker bars include a fin positioned in said gap beneath the ribbon to cooperate with said cut-off knife to cut the elastic ribbon.

9. Apparatus in accordance with claims 6 wherein said means for providing a supporting surface with gaps comprises a roller having a surface with spaced grooves which register in sequence with interfitting tucker bars.

10. A method for making disposable diapers comprising the steps of:
 (a) continuously moving a web of substantially inelastic material suitable as one of a backing and facing material through an elastic ribbon applying station;
 (b) forming transverse folds at spaced locations along said web;
 (c) feeding elastic ribbon under tension to said web;
 (d) applying adhesive to the elastic ribbon;
 (e) joining the stretched elastic ribbon with adhesive to said web and over the folds;
 (f) maintaining the elastic ribbon in a stretched condition until the adhesive sets;
 (g) severing the elastic ribbon where the ribbon crosses the folds;
 (h) removing the folds from the web to space apart the ends of the severed elastic ribbons and provide web portions without adhered elastic bands to form the waistband portions of the diapers;
 (i) applying an absorbent pad to the web;
 (j) superimposing and adhering the other of the backing and facing web to the pad assembly; and
 (k) severing the individual diapers from the web assembly, and wherein the unit length of the applied under tension elastic ribbon is less than the unit length of the diaper.

* * * * *